United States Patent
Ahmad et al.

[11] Patent Number: 5,187,971
[45] Date of Patent: Feb. 23, 1993

[54] CALIBRATION CUVETTE

[75] Inventors: Jamil Ahmad, Vista; Samuel D. Riccitelli, Murrieta, both of Calif.

[73] Assignee: Puritan-Bennett Corporation, Carlsbad, Calif.

[21] Appl. No.: 565,463

[22] Filed: Aug. 10, 1990

[51] Int. Cl.⁵ .................... G01D 18/00; G01N 21/03
[52] U.S. Cl. .................... 73/1 G; 356/243; 356/246
[58] Field of Search ............... 73/1 G, 1 R; 436/8–19; 356/246, 243; 250/252.1 R, 252.1 A, 227.14

[56] References Cited

U.S. PATENT DOCUMENTS

| | | | |
|---|---|---|---|
| D. 302,299 | 7/1989 | Long et al. | D24/29 |
| 3,286,583 | 11/1966 | Ferrari | 356/246 |
| 3,345,910 | 10/1967 | Rosin et al. | 356/246 X |
| 3,430,041 | 2/1969 | Kaye | 356/246 X |
| 3,431,424 | 3/1969 | Allen | 356/246 X |
| 3,545,864 | 12/1970 | Dibbern | 356/246 X |
| 3,622,795 | 11/1971 | Dorman, Jr. et al. | 356/246 X |
| 3,751,167 | 8/1973 | Claus | 356/246 X |
| 3,802,786 | 4/1974 | Anderson et al. | 356/246 |
| 3,881,827 | 5/1975 | Gilford et al. | 356/246 |
| 4,076,420 | 2/1978 | DeMaeyer et al. | 356/246 X |
| 4,111,560 | 9/1978 | Jolanki et al. | 356/243 X |
| 4,221,567 | 9/1980 | Clark et al. | 128/635 X |
| 4,236,820 | 12/1980 | Walker | 356/244 X |
| 4,253,845 | 3/1981 | Smernoff | 422/99 X |
| 4,266,941 | 5/1981 | Sullivan | 73/1 G X |
| 4,301,117 | 11/1981 | Smernoff | 422/99 |
| 4,567,748 | 2/1986 | Klass et al. | 73/1 G |
| 4,739,645 | 4/1988 | Drbal | 73/1 G |

Primary Examiner—Tom Noland
Attorney, Agent, or Firm—Fulwider, Patton, Lee & Utecht

[57] ABSTRACT

The calibration cuvette apparatus for storing and calibrating a chemical sensor in a tonometered solution includes an upper cuvette section and a lower cylindrical valve section for alternately sealing the cuvette section and admitting a gas mixture to the cuvette section. The upper cuvette section has relatively narrow diameter upper and lower ends on either side of a wide diameter middle portion. The cuvette section is adapted to receive the sensor and retain the sensor in a fluid bath in the cuvette section so that the chemical sensor portion is disposed approximately in the center of the wide middle portion of the cuvette section. The chamber formed within the cuvette section is thus shaped so as to maintain the sensor in a position in the fluid bath so that any gas bubbles within the chamber will not dry the sensor. A lower end portion of the cuvette section includes a gas communication inlet for introducing gas into said chamber to equilibrate the tonometered buffer solution.

34 Claims, 1 Drawing Sheet

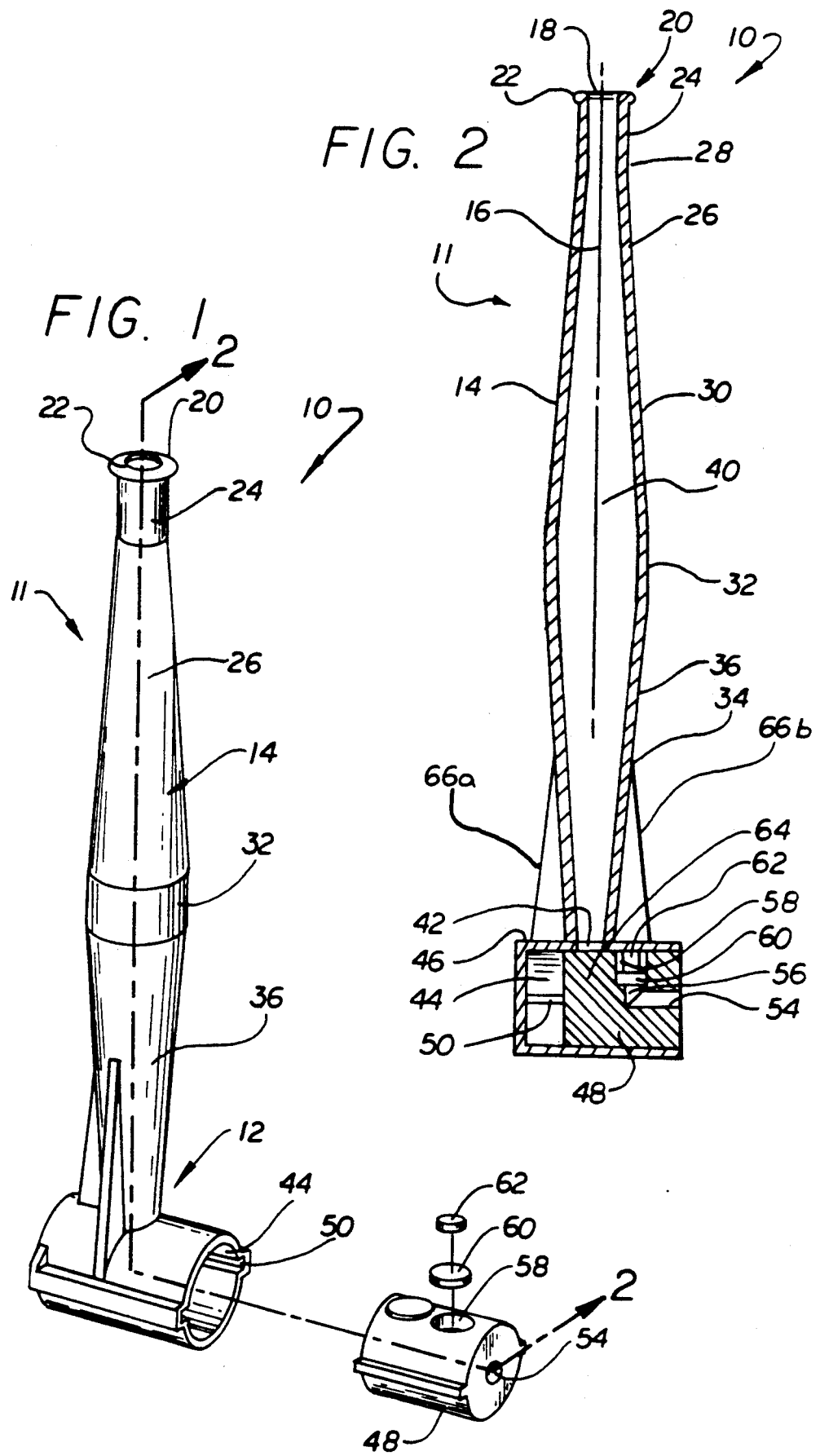

the cuvette section in the other valve position. The upper cuvette section has relatively narrow diameter upper and lower ends on either side of a wide diameter middle portion. The cuvette section is adapted to hold the chemical sensor in a fluid bath in the cuvette section so that the chemical sensor is disposed approximately in the center of the wide middle portion of the cuvette section. The chamber formed within the cuvette section is thus shaped so as to maintain the sensor in a position in the fluid bath so that any gas bubbles within the chamber will not dry the sensor. A lower end portion of the cuvette section includes a gas communication inlet for introducing gas into the chamber to equilibrate the tonometered buffer solution.

CALIBRATION CUVETTE

BACKGROUND OF THE INVENTION

Field of the Invention

This invention generally relates to calibration of analytical chemistry devices, and more particularly relates to a device for calibrating sensors for measuring gas concentrations and pH of a fluid.

Description of Related Art

In modern medicine, measurement of acidity (pH), and oxygen and carbon dioxide levels in the blood has become an important factor in the determination of the respiratory status of a patient. Although electrodes have been developed which are capable of measuring these blood factors in fluids, such electrodes are of limited use in measurement of in vivo blood pH levels. Optical sensors called "optodes" have been developed for taking intravascular measurements of acidity and other blood analytes such as oxygen and carbon dioxide. Such optical sensors typically include a fluorescent indicator dye placed over the tip of an optical fiber and covered by a membrane which is permeable to the chemical of interest.

It is frequently desireable to keep such sensors wet prior to use in an aqueous, tonometered buffer solution which is isotonically adjusted to match the ionic strength of the fluid of interest, such as blood. Such sensors must also be sterilized, such as in an autoclave, before they are used intravenously. The autoclaving process can cause pressure buildup in the buffer solutions, placing unusual stresses on the fluid container in which the sensor is sterilized to cause leakage of the container. It is also desirable to calibrate such sensors before use, and frequently several times daily, using tonometered sample liquids with known levels of the analyte of interest. One method of preparing an appropriate tonometered buffer solution involves bubbling a prepared gas mixture, such as of $CO_2$, $O_2$, and $N_2$ through the solution until equilibration of the gas mixture in the solution occurs. However, it has been found that drying of the membrane of the chemical sensor can occur where gas bubbles come in contact with the chemical sensor, affecting the performance of the sensor. It is also useful to provide a bio-filter in the gas bubbling apparatus to filter the gas mixture before it enters the solution, but it has been found that such filters can become clogged if exposed to the buffer solution for extended storage periods.

Accordingly, there remains a need for an apparatus that will allow storage of the sensor in an appropriate fluid to protect the sensor from drying out, that will provide a way of isolating the bio-filter from becoming clogged during a period of storage of the sensor in the fluid, and that will provide for good sealing of the sensor and fluid in the apparatus for the internal pressure which builds up in the fluid during the autoclaving process.

SUMMARY OF THE INVENTION

Briefly and in general terms, a calibration cuvette apparatus according to the present invention comprises an apparatus for storing and calibrating a chemical sensor in a tonometered buffer solution. The apparatus includes an upper cuvette section and a lower cylindrical valve section for sealing the cuvette section in one valve position, while allowing the admission of a gas mixture to the cuvette section in the other valve position. The upper cuvette section has relatively narrow diameter upper and lower ends on either side of a wide diameter middle portion. The cuvette section is adapted to hold the chemical sensor in a fluid bath in the cuvette section so that the chemical sensor is disposed approximately in the center of the wide middle portion of the cuvette section. The chamber formed within the cuvette section is thus shaped so as to maintain the sensor in a position in the fluid bath so that any gas bubbles within the chamber will not dry the sensor. A lower end portion of the cuvette section includes a gas communication inlet for introducing gas into the chamber to equilibrate the tonometered buffer solution.

The lower, generally tubular valve section is preferably formed integrally with the cuvette section with an axis extending perpendicular to the longitudinal axis of the cuvette section. A generally cylindrical elastomeric valve plug is disposed within the valve chamber, and is slidable between a first sealing position and a second gas communication position. The valve plug includes a gas communication channel with an inlet port at one of the ends of the valve plug and a gas outlet port at the outer circumference of the valve plug adapted to be aligned to be in communication with the cuvette gas communication inlet when the valve plug is in the gas communication position. The cuvette section is preferably formed in the shape of an elongated dual frustrum, with the cuvette section having an upper frustoconical portion and a lower frustoconical portion, with the wide diameter portion of the cuvette section located at the wide diameter portions of the two frustoconical portions. The gas communication channel also preferably includes a filter and a sparger for filtering the gas and dispersing the gas bubbles evenly within the cuvette section as it is introduced into the chamber of the cuvette.

Other aspects and advantages of the invention will become apparent from the following detailed description, taken in conjunction with the accompanying drawings, which illustrate, by way of example, the principles of the invention.

BRIEF DESCRIPTION OF THE DRAWINGS

FIG. 1 is a perspective view of the calibration cuvette apparatus of the invention; and FIG. 2 is a cross-sectional view taken along line 2—2 of FIG. 1.

DETAILED DESCRIPTION OF THE PREFERRED EMBODIMENT

As is shown in the drawings which are provided for purposes of illustration, and not by way of limitation, the invention is embodied in a calibration cuvette apparatus for storing and calibrating a chemical sensor in a tonometered solution. The apparatus has a unique shape which allows for storage and calibration of the sensor in an appropriate solution, protecting the sensor from extended contact with bubbles in the solution which could otherwise dry a portion of the sensor sufficiently to affect the performance of the sensor. The apparatus also provides a bio-filter for gas to be infused in the tonometered solution. The apparatus also includes a valve section for isolating the bio-filter from becoming clogged during a period of storage of the sensor in the solution and sealing the sensor and solution in the cuvette section of the apparatus during autoclaving of the apparatus.

Referring to FIG. 1, the present invention is embodied in a calibration cuvette apparatus 10 having a novel shaped cuvette section 11 adapted to receive a catheter having a chemical sensor portion. The general shape of the cuvette section is that of a dual frustrum designed to prevent the chemical sensor from contacting any bubbles that may form within a tonometered buffer solution in the cuvette section, to keep the chemical sensor of the catheter wet, in any position of the calibration cuvette apparatus, when the chemical sensor is inserted into the approximate middle of the cuvette section. The calibration cuvette apparatus also includes a lower generally cylindrical valve section 12 formed integrally with the housing 14 of the upper cuvette section. The housing of the calibration cuvette apparatus is preferably comprised of glass, in order to allow the retention of various gas mixtures, particularly in order to facilitate long term intravenous blood gas catheter storage in the calibration cuvette apparatus. Alternatively, it may be possible to form the housing of the calibration cuvette from a variety of plastics which may be suitable for retaining different gas mixtures.

As further illustrated in FIG. 2, the upper dual frustrum cuvette section is generally elongated and tubular in its side aspect, having a vertical, longitudinal axis 16. An aperture 18 is provided at the extreme upper luer end 20 for receiving the chemical sensor catheter. The upper end also preferably includes an upper cylindrical neck portion 24 connecting the mouth 22 of the luer end with the narrow upper end 28 of the upper frustoconical portion 26 of the cuvette section. The upper frustoconical portion gradually enlarges downwardly to form a relatively wider lower end 30 of the upper frustoconical portion contiguous with the wide diameter middle portion 32. The middle portion 32 is preferably formed in the shape of a short cylindrical tube, and extends downwardly to be contiguous with the wide diameter upper section 36 of the lower frustoconical portion 34 of the cuvette section. The diameter of the lower frustoconical portion gradually decreases downwardly to the narrow diameter and lower end 38 of the lower frustoconical portion.

The upper cuvette section thus forms a hollow, inner chamber 40 for receiving the chemical sensor catheter, such as an intravascular blood gas sensor, and maintaining the position of the chemical sensor in the approximate center of the widened middle portion of the upper cuvette section, in a bath of buffer solution. The narrow diameter lower end of the frustoconical portion of the cuvette section includes a lower aperture 42, which serves as a gas communication inlet for introducing gas mixtures formulated as desired into the buffer solution to maintain a desired proportion of dissolved gases in the solution for purposes of storage and calibration of the chemical sensor.

The lower cylindrical valve section includes a lower valve chamber 44 formed in the housing 46 of the cylindrical valve section, which is preferably formed integrally with the housing of the upper cuvette section. The valve section is generally cylindrical, having a horizontal longitudinal axis extending perpendicular to the vertical, longitudinal axis of the upper cuvette section. A generally cylindrical elastomeric, piston-type plug 48 is preferably disposed coaxially within the lower valve chamber, and is slidable within the valve chamber between the sealing position which is illustrated in FIG. 2, and a gas communication position. Although the plug is preferably formed of an elastomer, such as rubber or polyurethane, to form a seal at the cuvette section opening, the plug may be formed of other materials such as plastic or metal, with appropriate seals. In order to facilitate alignment of the elastomeric plug with the lower, gas communication aperture in the upper cuvette section in each of these two valve positions, the inner surface of the cylindrical valve housing includes one or more, and preferably two, alignment channels or grooves 50 adapted to receive corresponding ribs or ridges 52 on the elastomeric plug, extending in a longitudinal direction aligned with the axes of the valve chamber and elastomeric plug. Alternatively such grooves could be placed on the plug, and ridges on the inner wall of the valve chamber.

The elastomeric plug preferably also includes a gas communication channel 56 for receiving the specially formulated gas mixture to be introduced into the upper cuvette section. The gas communication channel includes a gas communication inlet 54 at one of the longitudinal ends of the elastomeric plug for receiving gas from an external supply, and an outlet end on the circumference of the elastomeric plug, which preferably includes a filter chamber 58. A biofilter 60 is preferably disposed in the filter chamber for filtering out undesirable particulate matter which may be carried along from an exterior gas supply line, and the filter chamber also preferably includes a frit, such as a thin glass frit 62 for sparging gas into the lower gas communication aperture 42 of the upper cuvette section, when the gas communication channel of the elastomeric plug is placed in its gas communication position aligned with the gas communication aperture of the cuvette section. Other materials which may be adapted for use in frit 62 include ceramics, polymerics or the like. Closely adjacent to the filter chamber on the circumference of the elastomeric plug is a sealing area 64 on the circumference of the elastomeric plug, adapted to be aligned with the opening in the cuvette section to seal the cuvette section in the valve sealing position during autoclaving and storage. Support structures, such as the fins 66a and 66b, may also be formed along with the housing to connect the upper housing of the cuvette section with the lower housing of the valve section, to provide added support and strength to the narrow diameter connection of the cuvette section to the cylindrical valve section.

It will be apparent to those skilled in the art from the foregoing that the calibration cuvette apparatus will maintain a seal around the sealing area of the elastomeric plug against the internal pressure of the cuvette solution caused by the elevated temperatures which occur during autoclaving, and that the biofilter will be isolated and protected during autoclaving and storage when the elastomeric plug of the valve is disposed in its sealing position. It is also significant that the elastomeric plug of the valve section can slide to a gas communication position to align the biofilter and sparger frit with the opening in the cuvette section to the solution through which a gas mixture can be bubbled when the chemical sensor in the cuvette section is to be calibrated. Due to the novel dual frustrum shape of the cuvette section, gas bubbles in the solution in the cuvette section will either dissolve in the solution, rise to the upper end of the cuvette section when the cuvette section is disposed vertically, or rise to the wide diameter middle section of the cuvette section if the cuvette section is placed horizontally. Thus, a chemical sensor placed in the approximate middle of the cuvette section will be protected from any gas bubbles in the solution within the cuvette section, and drying of the chemical sensor, either during calibration or storage will be prevented. It is also significant that the biofilter and sparger frit in the elastomeric plug can be kept isolated from the solution in the upper cuvette section during a storage period and before calibration of a chemical sensor, so that particulate matter within the solution will not clog the sparger or biofilter.

While particular forms of invention have been illustrated and described, it will be apparent that various modifications can be made without departing from the spirit and scope of this invention. Accordingly, it is not intended that the invention be limited, except as by the appended claims.

What is claimed is:

1. A calibration cuvette apparatus having a housing adapted to contain a calibration fluid and to receive a chemical sensor, said calibration cuvette apparatus comprising:
   a generally tubular cuvette section having a longitudinal axis formed in said housing, said cuvette section having a hollow chamber with upper, middle and lower portions, said upper and lower portions having a relatively smaller inner diameter than said middle portion, said upper end portion having an opening for receiving said sensor;
   a valve section formed in said housing integrally with said cuvette section for introducing gas into said cuvette chamber, said valve section having first and second longitudinal end portions, a gas communication port extending between said cuvette chamber and an inner valve chamber extending between said valve section end portions; and
   a valve plug slidable within said valve chamber between a first sealing position and a second gas communication position, said valve plug having first and second longitudinal ends and an outer circumference portion, and said valve plug having a gas communication channel with an inlet port at one of said valve plug ends and a gas outlet port at said outer circumference portion adapted to be aligned to be in communication with the cuvette gas communication port when said valve plug is in said gas communication position.

2. The apparatus of claim 1, wherein said cuvette section is formed in the shape of an elongated dual frustrum, with said cuvette section comprising an upper frustoconical portion including said narrow upper end portion and a wide diameter lower end portion contiguous with said middle portion, and a lower frustoconical portion including a wide diameter upper end portion contiguous with said middle portion and said narrow lower end portion.

3. The apparatus of claim 1, wherein said narrow upper end portion of said cuvette section includes a cylindrical neck portion adapted for receiving said sensor.

4. The apparatus of claim 1, wherein said wide diameter middle portion of said cuvette section comprises a generally cylindrical, tubular section.

5. The apparatus of claim 1, wherein said narrow upper end portion of said cuvette section includes a catheter luer fitting for receiving said sensor.

6. The apparatus of claim 1, wherein said valve chamber portion is in communication with said cuvette gas communication port.

7. The apparatus of claim 1, wherein said valve section and said valve plug include means for aligning said valve plug within said valve chamber.

8. The apparatus of claim 7, wherein said means for aligning said valve plug within said valve chamber comprises tongue and groove means including at least one rib on one of said valve plug and said valve section and at least one corresponding groove adapted to interfit with said rib on the other of said valve plug and said valve section.

9. The apparatus of claim 1, wherein said valve plug gas communication channel includes means for filtering said gas mixture.

10. The apparatus of claim 9, wherein said means for filtering said gas mixture comprises a biofilter.

11. The apparatus of claim 9, wherein said means for filtering said gas mixture comprises means for sparging gas into said cuvette section.

12. The apparatus of claim 1, wherein said chamber in said cuvette section contains said fluid, and said valve plug gas communication channel includes means for dispersing said gas in said fluid.

13. A calibration apparatus adapted to contain a calibration fluid and to receive a chemical sensor, said calibration apparatus comprising:
   an upper elongated, generally tubular dual frustrum shaped cuvette section, said cuvette section having a longitudinal axis, said cuvette section having relatively small diameter upper and lower end portions compared to the diameter of a middle portion of said cuvette section, said upper, lower, and middle portions of said cuvette section forming a hollow chamber within said cuvette section, said upper portion having an opening for receiving said sensor, and said lower portion including a gas communication inlet for introducing gas into said chamber;
   a valve section for selectively introducing a gas into said hollow chamber formed integrally with said cuvette section, said valve section having first and second longitudinal end portions, an axis extending between said end portions, and an inner valve chamber; and
   a valve plug moveable within said valve chamber between a first sealing position and a second gas communication position, said valve plug having a gas communication channel and a gas outlet port adapted to be aligned to be in communication with the cuvette gas communication inlet when said valve plug is in said gas communication position.

14. The apparatus of claim 13, wherein said valve plug includes sealing means for sealing said gas communication inlet when said valve plug is in said sealing position.

15. The apparatus of claim 13, wherein said valve plug gas communication channel includes means for filtering said gas mixture.

16. The apparatus of claim 15, wherein said means for filtering said gas mixture comprises a biofilter.

17. The apparatus of claim 13, wherein said valve section and said valve plug include means for aligning said valve plug within said valve chamber.

18. The apparatus of claim 17, wherein said means for aligning said valve plug within said valve chamber comprises tongue and groove means including at least one rib on one of said valve plug and said valve section and at least one corresponding groove adapted to interfit with said rib on the other of said valve plug and said valve section.

19. The apparatus of claim 13, further comprising means for dispensing said gas into said gas communication inlet.

20. A calibration cuvette apparatus having a housing adapted to contain a calibration fluid and to receive a chemical sensor to be immersed in said calibration fluid, said calibration cuvette apparatus comprising:
   a hollow cuvette section having a longitudinal axis formed in said housing, said cuvette section having an inner chamber with an upper end portion, a middle portion, and a lower end portion including means for introducing gas into said chamber, said upper end portion having means for disposing said sensor substantially centrally within said middle portion, and said hollow cuvette section having an inside diameter which is relatively larger at said middle portion than at said upper and lower end portions such that gas bubbles in said middle portion will not dry said sensor;
   said means for introducing gas into said chamber including a valve section in said lower portion of said cuvette section, said valve section having an inner valve chamber with first and second longitudinal open end portions, and a gas communication port permitting fluid communication between said cuvette chamber and said inner valve chamber; and
   a valve plug slidable within said valve chamber between a first sealing position and a second gas communication position, said valve plug having first and second longitudinal ends and an outer circumference portion, and said valve plug having a gas communication channel with an inlet port at one of said valve plug ends and a gas outlet port at said outer circumference portion adapted to be aligned to be in communication with the cuvette gas communication port when said valve plug is in said gas communication position.

21. The apparatus of claim 24, wherein said upper end portion of said cuvette section includes a catheter luer fitting for receiving said sensor.

22. The apparatus of claim 24, wherein said valve chamber portion is in communication with said cuvette gas communication port.

23. The apparatus of claim 24, wherein said valve section and said valve plug include means for aligning said valve plug within said valve chamber.

24. The apparatus of claim 23, wherein said means for aligning said valve plug within said valve chamber comprises tongue and groove means including at least one rib on one of said valve plug and said valve section and at least one corresponding groove adapted to interfit with said rib on the other of said valve plug and said valve section.

25. The apparatus of claim 20, wherein said valve plug gas communication channel includes means for filtering said gas mixture.

26. The apparatus of claim 25, wherein said means for filtering said gas mixture comprises a biofilter.

27. The apparatus of claim 25, wherein said means for filtering said gas mixture comprises means for sparging gas into said cuvette section.

28. The apparatus of claim 20, wherein said chamber in said cuvette section contains said fluid, and said valve plug gas communication channel includes means for dispersing said gas in said fluid.

29. A calibration apparatus adapted to contain a calibration fluid and to receive a chemical sensor, said calibration apparatus comprising:
   an upper elongated, generally tubular dual frustrum shaped cuvette section, said cuvette section having a longitudinal axis and a hollow inner chamber with an upper end portion, a lower end portion, and a middle portion, said hollow inner chamber having an inner diameter which is relatively smaller in said upper and lower end portions than in said middle portion, said upper end portion having an opening for receiving said sensor, and said lower end portion including a gas communication inlet for introducing gas into said hollow inner chamber;
   valve means connected to said lower end portion operative to selectively introduce a gas through said gas communication inlet into said hollow inner chamber;
   said valve means including a valve housing section connected with said cuvette section, said valve housing section having first and second longitudinal end portions, an axis extending between said end portions, and an inner valve chamber; and
   a valve plug moveable within said valve chamber between a first sealing position and a second gas communication position, said valve plug having a gas communication channel and a gas outlet port adapted to be aligned to be in communication with the cuvette gas communication inlet when said valve plug is in said gas communication position.

30. The apparatus of claim 29, wherein said valve plug includes sealing means for sealing said gas communication inlet when said valve plug is in said sealing position.

31. The apparatus of claim 29, wherein said valve plug gas communication channel includes means for filtering said gas mixture.

32. The apparatus of claim 31, wherein said means for filtering said gas mixture comprises a biofilter.

33. The apparatus of claim 29, wherein said valve section and said valve plug include means for aligning said valve plug within said valve chamber.

34. The apparatus of claim 33, wherein said means for aligning said valve plug within said valve chamber comprises tongue and groove means including at least one rib on one of said valve plug and said valve section and at least one corresponding groove adapted to interfit with said rib on the other of said valve plug and said valve section.

* * * * *